Figure 1:
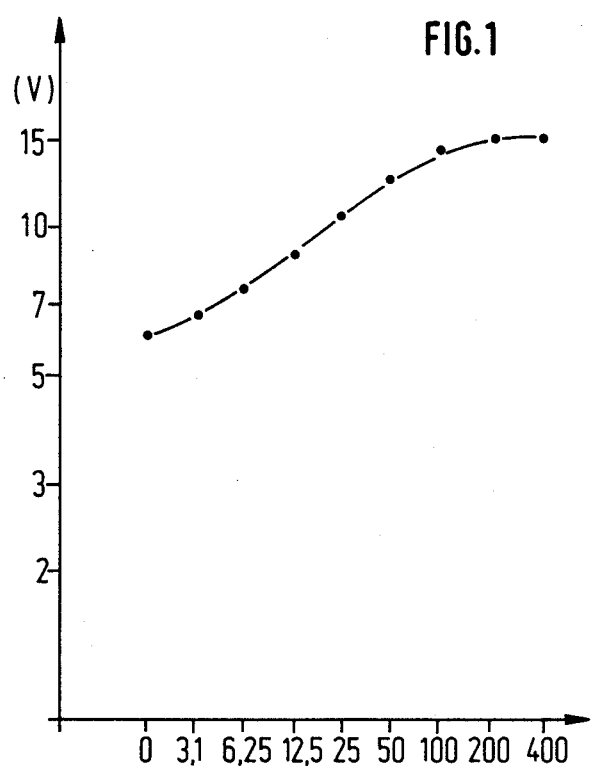

United States Patent [19]

Kapmeyer et al.

[11] Patent Number: 4,945,146
[45] Date of Patent: Jul. 31, 1990

[54] DISPERSION POLYMERS PROCESSES FOR THEIR PREPARATION AND THEIR USE

[75] Inventors: Wolfgang Kapmeyer, Marburg; Helmut Rinno, Hofheim am Taunus, both of Fed. Rep. of Germany

[73] Assignee: Behringwerke Aktiengesellschaft, Marburg/Lahn, Fed. Rep. of Germany

[21] Appl. No.: 124,338

[22] Filed: Nov. 18, 1987

Related U.S. Application Data

[63] Continuation of Ser. No. 943,802, Dec. 29, 1986, abandoned.

[30] Foreign Application Priority Data

Dec. 21, 1985 [DE] Fed. Rep. of Germany ....... 3545595

[51] Int. Cl.$^5$ .......................................... C08F 265/10
[52] U.S. Cl. ..................... 526/304; 524/458; 525/296; 436/533; 436/534
[58] Field of Search ........... 524/458; 525/296; 525/304; 436/533, 534

[56] References Cited

U.S. PATENT DOCUMENTS

| | | | |
|---|---|---|---|
| 3,796,773 | 3/1974 | Coleman | 525/296 |
| 4,210,723 | 7/1980 | Dorman et al. | 436/534 |
| 4,448,908 | 5/1984 | Pauly | 523/201 |
| 4,563,431 | 1/1986 | Pauly | 525/296 |

*Primary Examiner*—Paul R. Michl
*Assistant Examiner*—Lee C. Wright
*Attorney, Agent, or Firm*—Finnegan, Henderson, Farabow, Garrett and Dunner

[57] ABSTRACT

The invention relates to dispersion polymers, processes for their preparation, and their use, and also active dispersion polymers (latex conjugates) prepared therefrom, the dispersion polymers being obtained by polymerizing compounds of the formula I $$H_2C=C(R_1)-CO-NH-(CH_2)_n-CH(OR_2)(OR_3) \qquad I$$

in which
n denotes 1–6;
$R_1$ denotes H or $CH_3$ and
$R_2$ and $R_3$ are identical or different and denote $-(CH_2)_m-CH_3$,
m denotes 0–7, or $-CY(X)(Z)$, in which X, Y and Z denote $(CH_2)_pCH_3$ and
p denotes 1–3, where X, Y and Z are identical or different, and compounds of the formula II $$H_2C=C(R_1)-CO-R-(CH_2)_n-(CHOH)\text{-}_m-(CH_2)_l-H \qquad II$$

in which
R denotes O or NH;
n denotes 1–3;
m denotes 1–4;
l denotes 0–4; and
$R_1$ denotes H or $CH_3$, with one another in the presence of a seed dispersion, whereby the copolymer is formed on the surface of the latex particles.

Latex conjugates are obtained therefrom by bonding the interesting antibodies or antigens to the dispersion polymers according to the invention.

13 Claims, 5 Drawing Sheets

DISPERSION POLYMERS PROCESSES FOR THEIR PREPARATION AND THEIR USE

This application is a continuation, of application Ser. No. 943,802, filed Dec. 19, 1986, now abandoned.

The invention relates to dispersion polymers, processes for their preparation, and their use, the dispersion polymers comprising latex particles whose outer layer forms a copolymer of vinyl monomers of which one is a hydroxyl group-carrying N-alkyl acrylamide compound or a corresponding methacrylate. Biologically active dispersion polymers are obtained from this by bonding biologically active substances which have free amino groups to reactive groups, derived from the aldehyde function, on the surface of the dispersion polymer particles according to the invention. These biologically active latex conjugates are suitable for serological and immunological determination processes.

It is known that the sensitivity of serological and immunological determination processes can be increased by using indicator or carrier particles which are charged with the appropriate immunological reagent. Red blood corpuscles or cells of a cell culture, for example may be used as carrier material. Latex particles having a diameter of 0.02 to 5 $\mu$m can also be employed for this.

It is furthermore known that polyhydroxy compounds, such as sugars or dextrans, can be used for coating a latex (European Patent No. 0,001,223, Hoffmann La Roche). Such Latexes are not stable towards detergent-containing buffers, since the polyhydroxy compounds bonded adsorptively may be separated from the Latex by such buffers.

European Patent Application EP-A No. 82,110,273.8 discloses latex particles which contain acetal functions bonded via acid amide groups. Latex nuclei, preformed in an aqueous medium, are slightly swollen using vinyl monomers which contain acetal functions bonded via acid amide groups, and these vinyl monomers, which must be sufficiently insoluble in water, are then copolymerized together with further monomers which may be of a hydrophilic or ionic nature. Such reagents can be employed for the nephelometric determination of C-reactive protein. For this purpose, serum samples are greatly diluted with buffer, normally 1:100, whereby interfering serum proteins, which would otherwise lead to false positive or false negative results, can be neglected. This procedure is possible since, in general, concentrations of C-reactive protein of more than 5 mg/liter must be present for diagnostic purposes. However, if it is desired to measure the concentration of trace proteins in the range from 1 $\mu$g/liter to 50 $\mu$g/liter the samples may not be correspondingly greatly diluted with buffer, since the concentration of the protein to be detected otherwise becomes so low that the detection sensitivity is not sufficient.

The detection sensitivity for latex preparations according to the state of the art cannot, however, be easily increased, and does not supply tests which function satisfactorily, for example, for the determination of immunoglobulin E. Attempting to increase the sensitivity leads to the signals for the measurement of a reference curve increasing unspecifically, after a relatively short time, in such a fashion that evaluation is no longer possible. There is no longer a steep reference curve. The reason is that the individual particles of such an unstable reagent agglutinate together without the presence of antigen.

Surprisingly, it has now been found that the disadvantages described of the state of the art can be overcome by using carrier particles which are prepared by copolymerizing preformed latex nuclei in an aqueous medium with acrylic or methacrylic monomers which contain acetal functions bonded via acid amide groups together with acrylic or methacrylic monomers which carry one or more hydroxyl groups.

The invention therefore relates to dispersions which contain carrier particles which comprise latex, and on whose surface a copolymer is located which is prepared from monomers having terminal acetals of the formula I

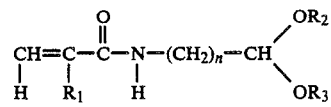

in which
n denotes 1–6;
$R_1$ denotes H or $CH_3$, and
$R_2$ and $R_3$ are identical or different and denote
—$(CH_2)_m$—$CH_3$,
m denotes 0–7, or

in which
X, Y and Z denote $(CH_2)_p CH_3$, and
p denotes 1–3, where X, Y and Z are identical or different,
and monomers of the formula II

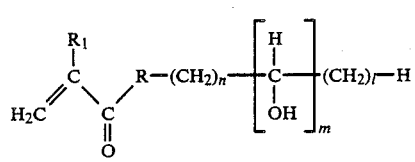

in which
R denotes 0 or NH;
n denotes 1–3;
m denotes 1–4;
l denotes 0–4; and
$R_1$ denotes H or $CH_3$,
in an aqueous medium.

The dispersions (or latexes) according to the invention can be prepared as a seed dispersion, which can be obtained as homo- or copolymers from monomers by means of known processes, by copolymerization on usual conventional latex particles.

The latex particles which are employed as the seed dispersion for the dispersions according to the invention should not be film-forming polymers. "Non film-forming" is taken to mean polymer latex particles which do not form a film under the application conditions suitable here and which do not coalesce. Polymers from carbocyclic aromatic monovinylidene monomers, such as styrene, vinyltoluene and vinylnaphthalene, and also mixtures of these monomers with one another and/or with methyl methacrylate and acrylonitrile are preferred. Particularly preferred seed dispersions are polystyrene latexes.

To prepare the modified seed latex according to the invention, about 20–80% of that amount of an emulsifier which would be necessary for maximum monomolecular coverage of the latex surface are added, in principle, to a preformed latex having particle diameters from 0.02 to 2 μm, preferably 0.05 to 0.5 μm. Measurements for the determination of the amount of emulsifier which leads to maximum coverage of the latex surface are carried out using a tensiometer. They have been published, for example, by I. Phrma and S. R. Chen in Journal of Colloid and Interface Science, Vol. 74 (1979), p. 90–102 and, for the first time, by S. H. Maron, M. E. Elder and I. N. Ulevitch in Journal of Colloid Interface Sciences, Vol. 9 (1954), p. 89–104.

Suitable emulsifiers are, for example, polyglycol ethers, having long-chain, aliphatic alcohols which preferably have 10–20 carbon atoms, or alkylphenol whose alkyl radical preferably contains 6–12 carbon atoms, or dialkylphenols or trialkylphenols whose alkyl radicals preferably represent branched alkyl radicals in each case having 3–12 carbon atoms. Examples of these are the products of reactions between ethylene oxide and lauryl alcohol, stearyl alcohol, oleyl alcohol, coconut fatty alcohol, octylphenol, nonylphenol, diisopropylphenol, triisopropylphenol, di-t-butylphenol and tri-t-butylphenol. Products of the reaction between ethylene oxide and polypropylene glycol or polybutylene glycol are also suitable.

Of the ionic emulsifiers, anionic emulsifiers are, above all, suitable, particularly alkyl or amonium salts of alkyl sulfonates, aryl sulfonates or alkylaryl sulfonates, and also of the corresponding sulfates, phosphates or phosphonates which optionally have oxyethylene units between the respective hydrocarbon radical and the anionic group. Examples of these are sodium dodecyl sulfate, sodium lauryl sulfate, sodium octylphenol glycol ether sulfate, sodium dodecylbenzenesulfonate, sodium lauryl diglycol sulfate, ammonium tri-t-butylphenol pentaglycol sulfate and ammonium tri-t-butylphenol octaglycol sulfate. Sodium dodecyl sulfate is preferably employed.

The polymerization is carried out by processes known per se in the presence of a radical-generating initiator, for example a peroxide compound or an aliphatic azo compound. The initiator to be employed is preferably water soluble; it is employed in an amount from 0.05 to 10% by weight, preferably 0.1 to 3% by weight (based on the total amount of monomers). Known radical-generating initiators are, for example, hydrogen peroxide, alkali or amonium salts of peroxodisulfuric acid or peroxodiphosphoric acid, for example sodium peroxodisulfate, potassium peroxodisulfate and ammonium peroxodisulfate, furthermore alkyl hydroperoxides such as t-butyl hydroperoxide, dialkyl peroxides such as di-t-butyl peroxide, diacyl peroxides such as diacetyl peroxide, dilauroyl peroxide and dibenzoyl peroxide, and also azodiisobutyronitrile, azodicarboxamide and azo-gamma,gamma'-bis(4-cyanovaleric acid). The alkali metal or ammonium salts of peroxodisulfuric acid, such as sodium, potassium and ammonium peroxodisulfate, are preferably employed.

The initiator is, if appropriate, employed together with a reducing agent, particularly with an alkali salt or alkaline earth metal salt of a reducing sulfur-containing acid; preferably suitable are sulfites, bisulfites, pyrosulfites, dithionites, thiosulfates and formaldehyde sulfoxylates. Glucose and ascorbic acid can also be used.

The monomer mixture of hydroxyl group-containing monomer of the formula II and acetal group-containing monomer of the formula I is added dropwise, with stirring, to the seed dispersion, which contains emulsifier and free-radical initiator. The temperature of the dispersion is between +10° and +120° C., preferably between +50° and +90° C.

The polyhydroxy compounds of the formula II are suitable as hydroxyl group-containing monomer. Mono- or dihydroxyalkylacrylic or methacrylic compounds are preferably empolyed. Particularly preferred are N-2,3-dihydroxypropylmethacrylamide, N-2-hydroxypropylmethacrylamide, 2-hydroxypropyl methacrylate and the corresponding acrylic compounds.

The compounds of the formula I are employed as acetal group-containing monomers, acrylamidoalkyl or methacrylamidoalkyl aldehyde dialkyl acetal where alkyl denotes $C_2$ to $C_8$ being used preferably. Very particularly suitable are acrylamido or methacrylamidoacetaldehyde di-n-pentyl acetal.

The monomers according to the formulae I and II are added to the seed dispersion as a mixture, the mixture of monomers comprising the polyhydroxy compound of the formula II in amounts from 10 to 90% by weight, preferably 30 to 70% by weight, and the acetal compound of the formula I in amounts from 90 to 10% by weight, preferably 70 to 30% by weight.

Up to 30% by weight, based on the total mixture, of styrene, vinylnaphthalene or vinyltoluene can be added to the mixture of monomers. In addition, the mixture of monomers can, if appropriate, also contain up to 30% by weight, based on the total mixture, of methacrylic acid, acrylic acid or crotonic acid.

Up to 20% by weight, based on the mixture of monomers, of dimethylformamide or other suitable substances which reduce the viscosity are advantageously added to the mixture comprising the monomers.

The mixture of monomers is added to the seed dispersion in amounts from 90 to 5% by weight, preferably 40 to 10% by weight, based on the total amount of seed dispersion and mixture of monomers.

The seed polymerization itself can be carried out by known processes. However, a preferred embodiment of the process according to the invention is the dispensing process, in which the mixture of monomers is added dropwise, with constant stirring, to the suspension of the latex nuclei under polymerization conditions, i.e. at a temperature of +10° to +120° C., preferably +50° to +90° C. The polymer is subsequently freed of excess monomers, remaining initiator, and emulsifier by known processes. The polymer is advantageously subjected to dialysis, for example against $NaHCO_3$ buffer (0.01 to 0.05% by weight).

For the preparation of the biologically active dispersions according to the invention, also described below as latex conjugate, the pH of a suspension of the seed-polymerized latex particles described above is adjusted to below 5, preferably below 3, and incubated with the immunologically active material to be bonded, such as, for example, antibodies or antigens. The labile bonds between an amino group of the protein and the liberated aldehyde on the latex particle according to the invention are reduced by known processes. A solution of sodium cyanoborohydride in neutral buffer is preferably used for this. If necessary, unbound immunologically active material or other contaminants are separated from the reaction batch. This is expediently carried out by centrifuging or washing on suitable membranes.

Figure 3:
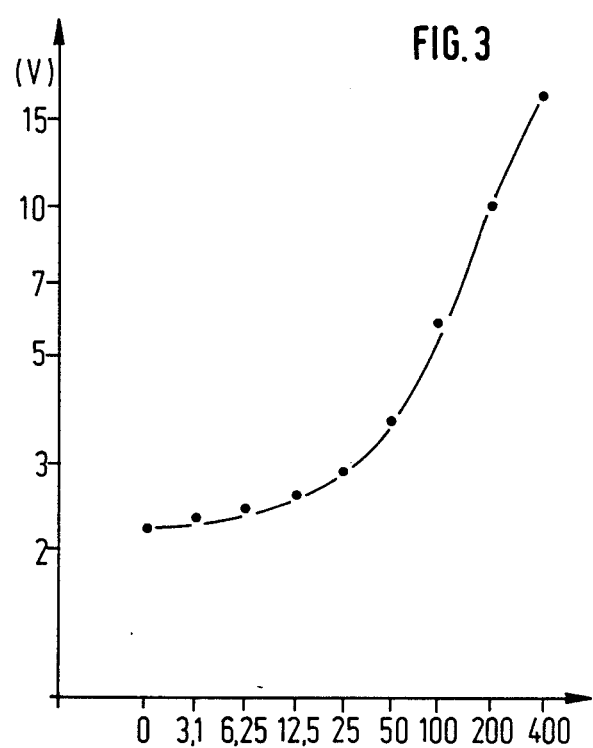

The seed-polymerized latexes according to the invention are distinguished by particular stability. They are suitable for the preparation of particularly sensitive reagents, whereas known dispersions, particularly those having a high detection sensitivity, tend to agglutinate non-specifically after a relatively short time. In the case of nephelometric or turbidimetric measurements, this leads to an increase in the scattered light or extinction signal. The signals for the measurement of a reference curve become so great after the reagent has been stored for several hours that evaluation is no longer possible. Such a change of the reference curve, recorded using a reagent according to the state of the art at different immunoglobulin E concentrations, is represented by FIG. 1. FIG. 3 represents the corresponding measurement, but carried out using the reagent according to the invention, prepared according to Example 3. It is clearly shown that the reagent according to the invention has a very much lower intrinsic agglutination, and its use leads to a broad, dynamic measuring range.

The stability of the latex reagent according to the invention is also demonstrated by the fact that it has a significantly lower reagent blank value than the reagent prepared according to the state of the art (cf. FIG. 3 and FIG. 1). Both after storage of the reagent for several months (up to at least 6 months) at +4° to +8° C. and on heat treatment of the lyophilized reagent at +37° C. for several days (up to at least 14 days), virtually unchanged results are obtained for a reference curve measured using different concentrations of immunoglobulin E.

Figure 2:
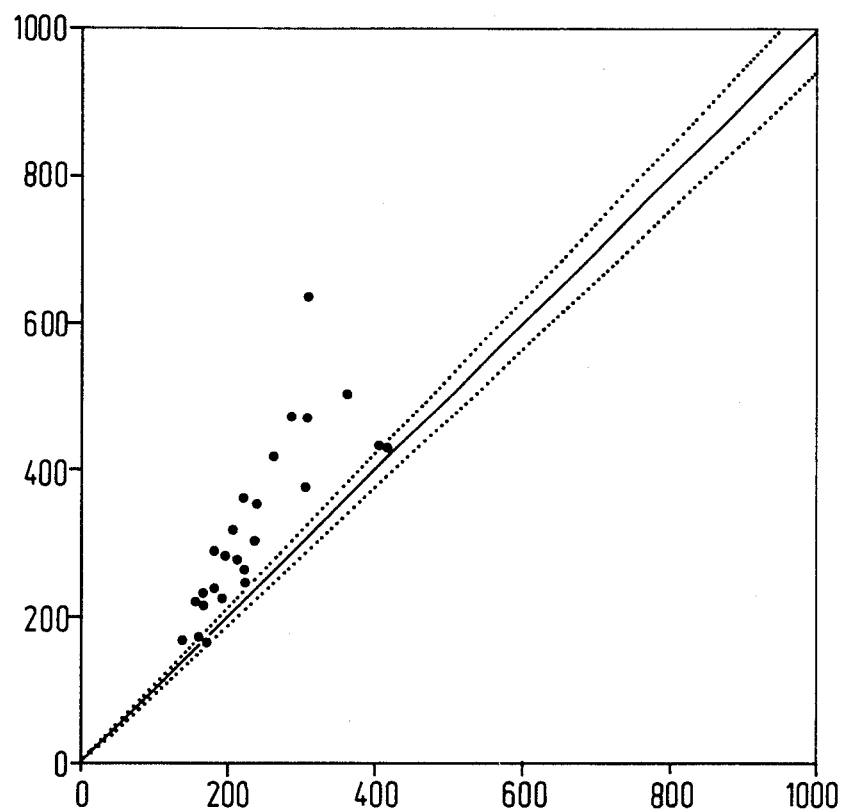
Figure 4:
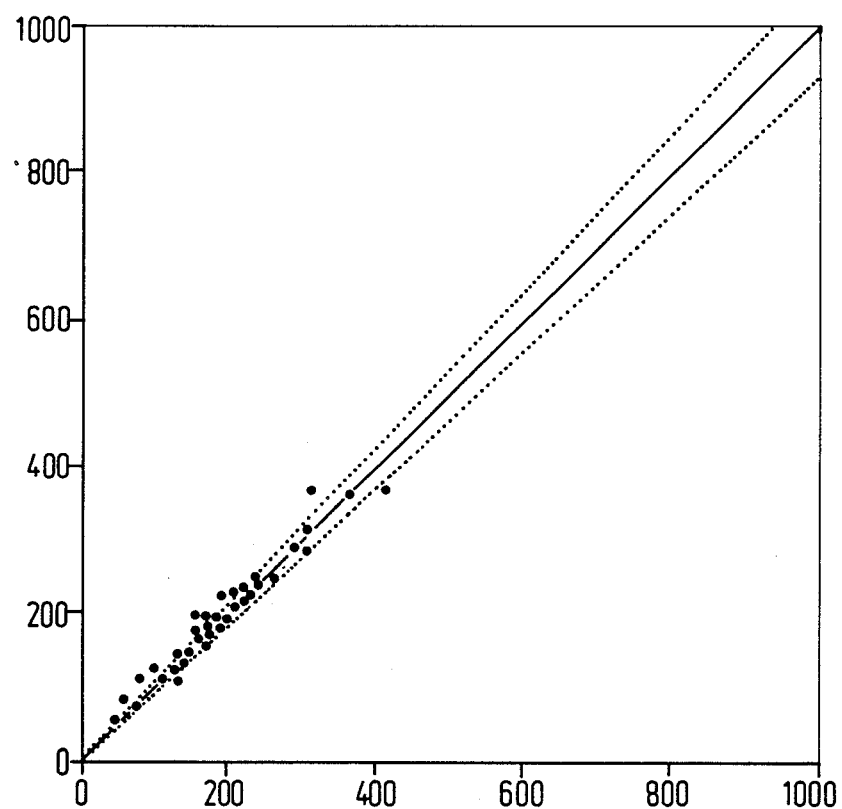
Figure 5:
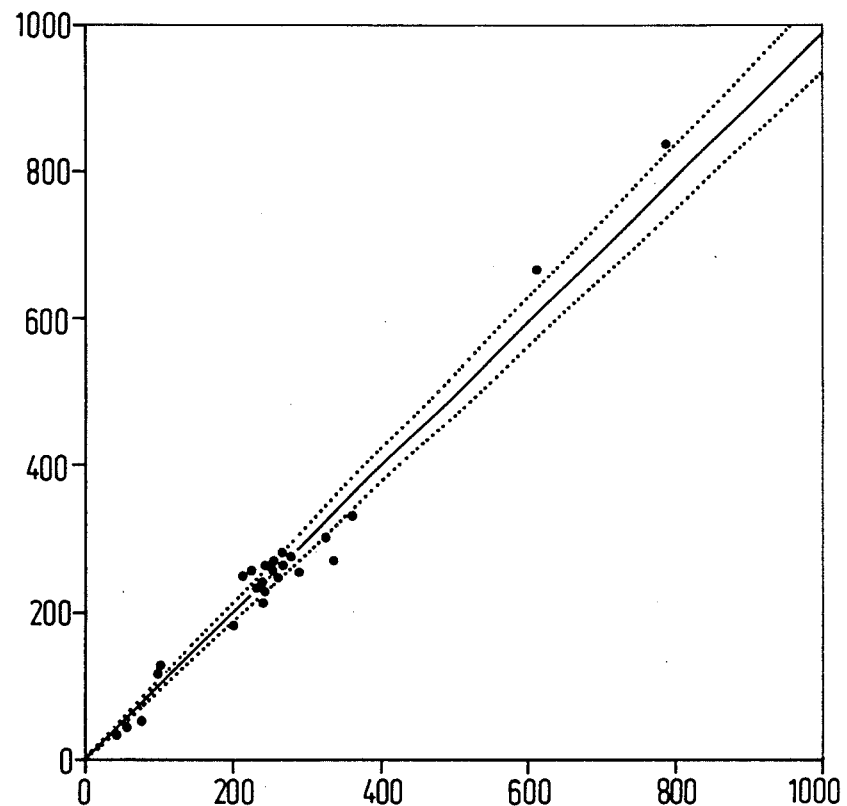

The disadvantages of conventional reagents are also shown by the fact that nephelometric or turbidimetric measurements carried out with them lead to results which do not agree well with those of an enzyme immunoassay. FIG. 2 shows the results of nephelometric measurements according to Example 5, according to the state of the art, for serum samples with an immunoglobulin E reagent, compared to results of enzyme immunoassays. The results of the identical nephelometric measurements, but carried out with an immunoglobulin E reagent using the latexes according to the invention, according to Examples 1 and 3, are represented by FIG. 4 and FIG. 5. As can be seen, excellent agreement with the results of the enzyme immunoassay is achieved.

Different values, depending on the serum matrix, are also obtained using the reagents according to the state of the art for different patient serums which do not contain their own immunoglobulin E, but have been augmented with the same amounts of purified immunoglobulin E. The results according to the invention also lead to marked improvements in this respect, as shown by a comparison of the measured values, collated in Table 1, with the measured values according to Table 2.

The latex preparations according to the invention are simple to prepare and can be linked gently with sensitive immunologically active materials to form a diagnostic reagent. The dispersion polymers according to the invention and their biologically active latexes prepared therefrom, the latex conjugates and reagents, are stable in comparison to those of the state of the art. They are insensitive to interferences caused by matrix effects, and nephelometric or tubidimetric measurements carried out with them lead to the results which can also be achieved using an enzyme immunoassay. In comparison to the state of the art, considerably fewer false positive or false negative results are obtained. By augmenting serums which are free of immunoglobulin E with purified immunoglobulin E, values are obtained using the reagent according to invention which vary little and are close to the theoretical value. The low susceptibility to interference effects is also shown by the low value of the variation coefficients (cf. Tables 1 and 2).

The latex conjugates can be employed in all diagnostic processes which measure particle size changes, for example in qualitative and semi-quantitative determinations of substances using visual latex agglutination tests, and also for nephelometric or turbidimetric determinations of trace proteins in the direct or competitive agglutination test or in the latex-hapten inhibition test.

EXAMPLES (1a) Synthesis of
N-(2,3-dihydroxypropyl)-methacrylamide 4.56 g of 3-amino-1,2-propanediol (0.05 mol) were dissolved in 30 ml of dimethylformamide (anhydrous). This solution, and also 13.8 g of $K_2CO_3$, were transferred to a 100 ml three-necked flask fitted with dropping funnel and gas inlet and gas outlet pipe. The mixture was cooled to 0° C. in an ice bath. 6.18 ml of methacryl chloride (0.06 mol), dissolved in 30 ml of dimethylformamide, were added dropwise over 30 minutes with moderate stirring and gentle passage of nitrogen. After stirring for a further hour with ice cooling, the mixture was allowed to warm to room temperature and was stirred for a further 30 minutes. The reaction batch was filtered through a fluted filter, and the residue was discarded. The filtrate was concentrated in a rotary evaporator until a viscous oil was produced. This oil was dissolved in 30 ml of methanol and filtered a second time, and the filtrate was again concentrated in a rotary evaporator. The residual amounts of solvent were removed in a high vacuum. The yield was 8.52 g.

(b) Polymerization of
N-(2,3-dihydroxypropyl)methacrylamide (NDPM) on polystyrene nuclei 22.3 ml of a polystyrene latex dispersion, having a solids content of 17.9% by weight, 57 ml of distilled water and 50 mg of sodium dodecyl sulfate were placed in a cylindrical glass vessel, fitted with gas inlet and gas outlet pipe and a magnetic stirring rod, and dissolved by stirring. The polymerization vessel was freed of oxygen by repeatedly evacuating and filling with nitrogen. The latex/detergent mixture was heated, with constant stirring, to +70° C. in a water bath. 1 ml of a potassium peroxodisulfate solution (16 mg/ml in distilled water) was added.

A mixture of monomers was prepared from 0.2 ml of styrene, 0.4 ml of methacrylamido acetaldehyde di-n-pentyl acetal, 0.025 ml of methacrylic acid and 0.4 ml of the N-(2,3-dihydroxypropyl)methacrylamide (NDPM) obtained in Example 1a), and also 0.2 ml of dimethylformamide, to improve the solubility of these monomers.

While stirring the polystyrene latex suspension vigorously, the mixture of monomers was slowly added dropwise over 60 minutes to the former. The temperature of the polymerization batch was maintained at 70° C. After the dropwise addition of the mixture of monomers, the mixture was stirred for a further 4 hours at the temperature mentioned. The polymerization was thus ended and the dispersion was cooled to room temperature and filtered through a fluted filter. 73 ml of a latex suspension were obtained. This was subsequently dialyzed for 17 hours against an NaHCO$_3$ buffer solution (0.25 g/liter, pH 8-8.2). 80 ml of a latex dispersion having a solids content of 4.7% by weight were obtained.

(2a) Synthesis of N-(2-hydroxypropyl)methacrylamide 3.75 g of 1-amino-2-propanol (0.05 mol) were placed in a three-necked flask, equipped with dropping funnel and gas inlet and gas outlet pipe, together with 30 ml of acetonitrile (anhydrous) and 13.79 g of K$_2$CO$_3$ (0.1 mol), and cooled to 0° C. in an ice bath. 6.18 g of methacryl chloride (0.06 mol), dissolved in 30 ml of acetonitrile, were added dropwise over 30 minutes with constant stirring and gentle passage of nitrogen. After stirring for a further 60 minutes with ice cooling, the mixture was allowed to warm to room temperature and was stirred for a further 30 minutes. The batch was filtered through a glass frit and the precipitate was discarded. The filtrate was concentrated in a rotary evaporator until a viscous oil was produced. This was dissolved in 30 ml of methanol and separated from any precipitate which appeared. The filtrate was again concentrated in a rotary evaporator and the residual amounts of the solvent were removed in a high vacuum. The yield was 6.66 g.

(b) Polymerization of N-(2-hydroxypropyl)methacrylamide on polystyrene nuclei

The polymerization was carried out similarly to that described in Example (1b). A mixture of 24.2 ml of polystyrene latex having a solids content of 16.5% by weight, 54.8 ml of distilled water and 50 mg of sodium dodecyl sulfate was prepared. This was placed in the polymerization vessel and the oxygen was removed. 1 ml of a potassium peroxodisulfate solution (16 mg/ml in distilled water) was added and the batch was heated to +70° C. A mixture of 0.4 ml of styrene, 0.4 ml of methacrylamido acetaldehyde di-n-pentyl acetal, 0.025 ml of methacrylic acid and 0.4 ml of N-(2-hydroxypropyl)methacrylamide was prepared.

The mixture of monomers was slowly added dropwise to the vigorously stirred polystyrene latex dispersion at +70° C. over 60 minutes. The mixture was subsequently stirred for a further 4 hours at the same temperature. After cooling to room temperature and filtration through a fluted filter, 74 ml of the polymer were obtained. This was subsequently dialyzed for about 20 hours against NaHCO$_3$ buffer (0.25 g/liter, pH 8-8.2). 79 ml of a latex suspension having a solids content of 5.4% by weight were obtained.

3. Polymerization of 2-hydroxypropyl methacrylate (HPM) on polystyrene nuclei

The polymerization was carried out similarly to that described in Example (1b). A mixture of 22.4 ml of polystyrene latex having a solids content of 17.9% by weight, 56.7 ml of distilled water and 50 mg of sodium dodecyl sulfate was prepared. This was placed in the polymerization vessel and the oxygen was removed. 1 ml of a potassium peroxodisulfate solution (16 mg/ml in distilled water) was then added and the batch was heated to +70° C. A mixture of 0.4 ml of styrene, 0.4 ml of methacrylamido acetaldehyde di-n-pentyl acetal, 0.025 ml of methacrylic acid and 0.2 ml of 2-hydroxypropyl methacrylate (HPM) was prepared. The mixture of monomers was slowly added dropwise to the vigorously stirred polystyrene latex suspension at +70° C. over 60 minutes. The mixture was subsequently stirred for a further 4 hours at the same temperature.

After cooling to room temperature and filtration through a fluted filter, 73 ml of the polymer were obtained. This was subsequently dialyzed for about 20 hours against NaHCO$_3$ buffer (0.25 g/liter, pH 8-8.2). 87 ml of a latex dispersion having a solids content of 5.1% were obtained.

4. Bonding of anti-immunoglobulin E antibodies to a polymer according to the invention Anti-immunoglobulin E antibodies were bonded to a polymer prepared using N-(2,3-dihydroxypropyl)methacrylamide according to Example 1 or prepared using N-(2,3-hydroxypropyl)methacrylamide according to Example 2 or prepared using 2-hydroxypropyl methacrylate according to Example 3.

The polymer employed in each case was diluted using distilled water to a solids content of 4% by weight. An anti-serum, obtained by immunization of rabbits using purified immunoglobulin E, was purified by known processes using affinity chromatography. It was subsequently concentrated until a protein content of 10 mg/ml had been reached.

3.4 ml of the abovementioned polymer were mixed with 0.34 ml of the anti-immunoglobulin E antibody solution. 0.17 ml of a 20% strength aqueous solution of eicosa-oxyethylene sorbitan laurate (®Tween 20) was then added and the whole was then mixed again. 0.05 ml of 1N HCl was added to this, so that a pH of about 2 was achieved. After an incubation time of 30 minutes at room temperature, 0.85 ml of saturated aqueous sodium hydrogen phosphate solution (pH 6.5) and 0.85 ml of aqueous sodium cyanoborohydride solution (25 mg/ml) were added and mixed thoroughly. The mixture was subsequently incubated for one hour at room temperature.

This preparation was then centrifuged for 30 minutes at about 50,000 g (Beckman centrifuge, 20,000 rpm). The supernatant liquid was discarded. The pellet was resuspended in 5 ml of a glycine/NaCl buffer (0.1 mol of glycine, 0.17 mol of NaCl, 0.5% of eicosa-oxyethylene sorbitan laurate (®Tween 20), pH 8.2).

The mixture was subsequently treated with ultrasound (Bronson Sonyfier B 15) for 2 seconds. The reagent thus redispersed was diluted in the volume ratio 1:80 with the abovementioned glycine/NaCl buffer.

5. Measurement of immunoglobulin E concentrations in serum samples

The reagent, prepared according to Example 4 by bonding anti-immunoglobulin E antibodies to latex preparations according to the invention, was employed for the measurement of immunoglobulin E in patient serums. The uppermost standard sample with the highest immunoglobulin E concentration of the enzygnost test (Behringwerke AG) is used as the standard. According to the packing insert, this immunoglobulin E standard contains 1,000 IU/ml. The standard was diluted further in twofold steps using a serum pool with no immunoglobulin E. A standard series was thus obtained with decreasing immunoglobulin E concentrations. The standard serums and the patient serums to be determined were diluted to 1:5 using a glycine/NaCl buffer (0.1/mol of glycine, 0.17 mol of NaCl, pH 8.2).

For the measurement, 20 μl of the patient serum dilution or the standard serum dilution were mixed with 150 μl of a reaction buffer (0.1 mol of glycine, 0.17 mol of NaCl, 4% of polyethylene glycol (PEG) 6000, 0.5% of ®Tween 20, pH 8.2) in BLN cuvettes (Behringwerke AG) and incubated for 30 minutes at room temperature. The cells were then measured in a laser nephelometer (Behringwerke AG). The reference curve for the measurement of the standard serums was plotted on semilogarithmic paper and the measured values for the patient serums were evaluated using this reference curve. A typical reference curve is represented in FIG. 3.

TABLE 1

Measured values in the nephelometric test, state of the art

| Serum No. | Concentration of immunoglobulin E in IU/ml |
|---|---|
| 1 | 441 |
| 2 | 399 |
| 3 | 556 |
| 4 | 416 |
| 5 | 431 |
| 6 | 425 |
| 7 | 454 |
| 8 | 398 |
| 9 | 422 |
| 10 | 356 |
| 11 | 315 |
| 12 | 382 |

Average value = 416 IU/ml = 80% reappearance
Nominal value = 520 IU/ml
Variation coefficient = 14%
Measured values in the nephelometric test according to Example 5 for serum samples which have been augmented with 520 IU/ml of immunoglobulin E in each case. The measurements were carried out using a reagent which was prepared according to the state of the art.

TABLE 2

Measured values in the nephelometric test, reagent according to the invention

| Serum No. | Concentration of immunoglobulin E in IU/ml |
|---|---|
| 1 | 435 |
| 2 | 516 |
| 3 | 609 |
| 4 | 537 |
| 5 | 526 |
| 6 | 571 |
| 7 | 608 |
| 8 | 559 |
| 9 | 589 |
| 10 | 542 |
| 11 | 559 |
| 12 | 450 |

Average value = 541 IU/ml = 104% reappearance
Nominal value = 520 IU/ml
Variation coefficient = 10%
Measured values in the nephelometric test according to Example 5 for serum samples which have been augmented with 520 IU/ml of immunoglobulin E in each case. The measurements were carried out using a reagent according to the invention, prepared according to Example 3.

We claim:

1. A process for preparing a dispersion polymer comprising the steps of:
   (a) adding an emulsifier and a free-radical initiator to an aqueous seed dispersion of latex having a particle diameter of 0.02 μm to 2 μm; and
   (b) adding dropwise with stirring at a temperature in the range of 10° C. to 120° C. to the seed dispersion containing the emulsifier and the initiator a monomer of Formula I $$CH=C-C-N-(CH_2)_n-CH\begin{matrix}OR_2\\OR_3\end{matrix}$$
$$\begin{matrix}|&|&\|&|\\H&R_1&O&H\end{matrix}$$

in which
   n denotes 1–6;
   $R_1$ denotes H or $CH_3$;
   $R_2$ and $R_3$ are identical or different and denote $-(CH_2)_m-CH_3$, and
   m denotes 0–7, or $$-C\begin{matrix}X\\Y\\Z\end{matrix},$$

in which
   X, Y and Z denote $(CH_2)_p-CH_3$ and
   p denotes 1–3, where
   X, Y and Z are identical or different, and a monomer of Formula II $$\begin{matrix}R_1\\|\\C\\\diagup\diagdown\\H_2C\quad C\\\|\\O\end{matrix}\quad R-(CH_2)_n-\left[\begin{matrix}H\\|\\C\\|\\OH\end{matrix}\right]_m-(CH_2)_l-H$$

in which
   R denotes O or NH;
   n denotes 1–3;
   m denotes 1–4;
   l denotes 0–4; and
   $R_1$ denotes H or $CH_3$
to form a dispersion polymer comprising latex particles and a copolymer of Formula I and II formed on the surface of the particle.

2. The process of claim 1, wherein mono- or di-hydroxyalkylacrylic or methacrylic compounds are employed as monomers of the formula II.

3. The process of claim 1, wherein at least one of the compounds N-2,3-dihydroxypropylmethacrylamide, N-2-hydroxypropylmethacrylamide, 2-hydroxypropyl methacrylate, N-2,3-dihydroxypropylacrylamide, N-2-hydroxypropylacrylamide or ethyl 2-hydroxypropylacrylate are employed as monomers of the formula II.

4. The process of claim 1, wherein acrylamidoalkyl or methacrylamidoalkyl aldehyde di-alkyl acetal wherein alkyl denotes $C_2$ to $C_8$ are employed as monomers of the formula I.

5. The process of claim 1, in which methacrylamido acetaldehyde di-n-pentyl acetal is used as monomers of the Formula I.

6. The process of claim 1, wherein the mixture of monomers contains, as the compound of the formula II, N-2,3-dihydroxypropylmethacrylamide, N-2-hydroxypropylmethacrylamide, 2-hydroxypropyl methacrylate or the corresponding acrylic compounds, and acrylamidoalkyl or methacrylamidoalkyl acetaldehyde di-n-pentyl acetal is employed as compound of the formula I.

7. The process of claim 1, wherein the mixture of monomers additionally contains up to 30% by weight, based on the total mixture, of styrene, vinylnapthalene or vinyltoluene.

8. The process of claim 1, wherein the mixture of monomers additionally contains up to 30% by weight, based on the total mixture, of methacrylic acid, acrylic acid or crotonic acid.

9. The process of claim 1, wherein the mixture of monomers contains, in addition to monomers of the formulae I and II, compounds from the group comprising styrene, vinylnapthalene or vinyltoluene, and one of the compounds methacrylic acids, acrylic acid or crotonic acid, and in addition up to 20% by weight, based on the total mixture, of dimethylformamide.

10. The process as claimed in claim 1, wherein the mixture of monomers contains, as compound of the formula II, mono- or dihydroxyalkylacrylic or methacrylic compounds, and acrylamidoalkyl or methacrylamidoalkyl aldehyde dialkyl acetal where alkyl denotes $C_2$ to $C_8$ is employed as compound of the formula I.

11. A biologically active dispersion polymer, comprising a dispersion polymer obtained by the process of claim 1 and an antibody, an antigen or a hapten bonded thereon.

12. A method of diagnostically detecting an antigen, an antibody or a hapten comprising the step of bonding a dispersion polymer obtained by the process of claim 1 to an antigen, an antibody, or a hapten to form a biologically active dispersion polymer.

13. The method of claim 12, further comprising the step of detecting the biologically active dispersion polymer by nephelometric, turbidimetric or particle counting methods.

* * * * *